United States Patent
Grob et al.

(10) Patent No.: US 6,451,614 B1
(45) Date of Patent: Sep. 17, 2002

(54) METHOD AND DEVICE FOR THE VAPORIZATION INJECTION

(75) Inventors: Konrad Grob, Fehraltorf (CH); Fausto Munari, Milan (IT); Sorin Trestianu, Rodano (IT); Paolo Magni, Besana Brianza (IT)

(73) Assignee: Thermoquest Italia, S.p.A., Rodano (IT)

( * ) Notice: Subject to any disclaimer, the term of this patent is extended or adjusted under 35 U.S.C. 154(b) by 149 days.

(21) Appl. No.: 09/588,400

(22) Filed: Jun. 6, 2000

(30) Foreign Application Priority Data

Jun. 11, 1999 (IT) .......................................... MI99A1298

(51) Int. Cl.[7] ............................................... G01N 30/02
(52) U.S. Cl. ......................... 436/161; 436/180; 422/70; 422/103; 95/87
(58) Field of Search .............................. 95/87; 73/23.41, 73/863.11; 436/161

(56) References Cited

U.S. PATENT DOCUMENTS

| | | | |
|---|---|---|---|
| 3,407,047 A | | 10/1968 | Lynn |
| 4,405,344 A | | 9/1983 | Sisti et al. |
| 4,474,588 A | * | 10/1984 | Hinshaw, Jr. ................ 96/105 |
| 4,615,226 A | | 10/1986 | Dinuzzo et al. |
| 5,252,109 A | * | 10/1993 | Munari et al. ................ 95/87 |
| 5,783,742 A | | 7/1998 | Shibamoto et al. |

FOREIGN PATENT DOCUMENTS

| | | |
|---|---|---|
| CH | 655 577 | 4/1986 |
| EP | 0 082 263 | 6/1983 |
| EP | 0011 1067 | 11/2000 |

* cited by examiner

*Primary Examiner*—Jill Warden
*Assistant Examiner*—Samuel P. Siefke
(74) *Attorney, Agent, or Firm*—Gibbons, Del Deo, Dolan Griffinger & Vecchione

(57) ABSTRACT

A method and device for vaporization injection in which there is at least one constriction between the end of the sample injection needle or tube and the interior of the heated vaporization chamber. The terminal part of the needle or tube can be heated to improve nebulisation of the sample and therefore its vaporization speed.

23 Claims, 1 Drawing Sheet

METHOD AND DEVICE FOR THE VAPORIZATION INJECTION

BACKGROUND OF THE INVENTION

Field of the Invention

This invention relates to a method and device for the injection of samples into the vaporization injector of a gas chromatography analysis apparatus.

Vaporization injectors are well-known in themselves. They are constituted by a vaporization chamber, usually in the form of a heated cylinder, connected at the bottom to the gas chromatography capillary column and closed at the top by a septum designed to be perforated by the sample injection needle. Said needle is fitted to a syringe containing a measured amount of sample, constituted by the substance to be analysed and usually by a solvent for said substance. When the needle is introduced it perforates the septum and penetrates to a predetermined position in the vaporization chamber. The liquid sample is forced by the syringe plunger into said chamber, where it vaporizes before being conveyed into the gas chromatography column by the carrier gas.

Depending on the procedure chosen, only part of the sample (split mode) or all the sample (splitless mode) is introduced into the column. In any event, it is important for the sample to vaporize thoroughly and for the whole within the vaporization chamber. Two different injection techniques have been used to comply with this requirement, both of which present drawbacks.

The first of these techniques, called "cold-fast injection", requires very rapid introduction of the needle and immediate expulsion of the liquid from the syringe so that when the injector head is maintained in relatively cold conditions, heating of the needle in the vaporization chamber, which is maintained at a high temperature, is limited, and does not cause vaporization of the sample in the needle. This technique ensures that the whole sample measured enters the vaporization chamber, preventing discrimination of high-boiling compounds in the needle but also creating a violent jet of liquid in the chamber which is difficult to vaporize. To aid vaporization, obstacles, usually glass wool, are placed in the chamber; the liquid is deposited on them and then vaporized. However, the material used for these obstacles tends to absorb part of the sample and cause it to degrade, thus distorting the analysis. In addition, the high introduction speeds necessarily require the use of an automatic sampler, as the operation cannot be performed manually in a sufficiently fast and reproducible manner. This means that manual and automatic injections are fundamentally different, and will produce different results.

The second technique currently used involves flash vaporization of the sample in the chamber and preheating of the sample in the needle. This technique requires the needle, emptied of the sample, to be left in the hot vaporization chamber for a period (e.g. 3–5 seconds) before the sample is injected. The period spent by the needle in the chamber increases the temperature in the needle, and this causes a violent evaporation of the part of the solvent in the sample, which passes into the heated part of the needle when the syringe plunger is lowered, thus creating high pressure which expels the liquid from the needle. As the sample is maintained in the syringe while the needle is empty before injection, distillation in the needle, which produces discrimination, can be minimised. On exit from the needle the liquid is sprayed in small droplets which immediately slow to the speed of the carrier, forming a mist. No packing or obstacle is therefore required to stop the jet of liquid. The drawback of this technique is that a very long needle is required, which creates dead volume because the volumetric quantity of the sample injected is not the quantity measured, as in the preceding case, but that quantity plus the volume of the needle.

Another drawback of both techniques is the presence of the septum which, being perforated by the needle, can introduce contaminant particles into the vaporization chamber.

OBJECTS AND SUMMARY OF THE INVENTION

That being said, an object of this invention is to offer a method and device for the vaporization injection of samples in a gas chromatography analysis apparatus which eliminates the drawbacks of the techniques currently used, in particular by optimising the conditions of introduction of the sample into the vaporization chamber, and therefore the conditions of vaporization of the sample, by a procedure involving dispersing the sample in the chamber, which gives rise to rapid vaporization of the sample, thus preventing the sample from remaining in the liquid state as far as possible.

The invention is also designed to prevent discrimination of the sample in the needle and to minimise the dead volume introduced by the needle into the measurement of the sample.

Finally, another object of the invention is to eliminate the drawbacks mentioned above, caused by the presence of the vaporization chamber closing septum, by enabling this septum to be eliminated.

The invention will now be described with reference to embodiments thereof which are illustrated by way of example in the annexed drawings, in which:

DESCRIPTION OF THE PREFERRED EMBODIMENTS

Figure 1:
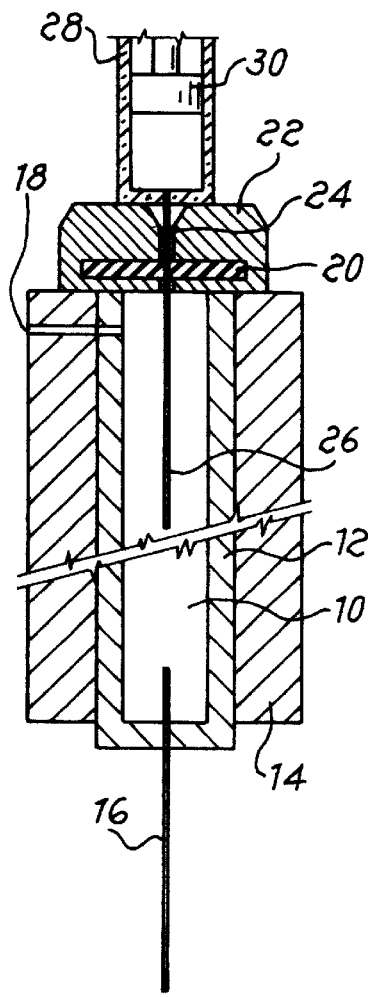
FIG. 1 is a schematic representation of an injection and vaporization device in accordance with the known technique

With reference to FIG. 1, a conventional vaporizer basically consists of a chamber 10, usually of an elongated cylindrical shape, with a liner 12, said chamber being heated independently by a device such as a resistor 14. The upstream end of a gas chromatography capillary column 16 is introduced into the bottom of chamber 10 in such a way as to form a seal. Reference 18 schematically indicates a carrier gas input. The vaporization chamber 10 is closed at the top by a perforatable septum 20, held in position by a covering element 22 including a guide 24 for the needle 26 of a syringe 28 having a piston or plunger 30.

The sample, constituted by a preset amount of the substance to be analysed and a solvent for said substance, is taken up with the syringe 28, needle 26 of which is then introduced into the guide 24, perforates the septum 20 and enters the vaporization chamber, into which the sample is introduced by pressing on plunger 30 in accordance with one of the two procedures described above. The sample-taking operation and the introduction of the sample into vaporization chamber 10 can be performed manually or with an automatic sampler. Penetration of the needle into chamber 10 is predetermined by a stop device which acts, for example, on the body of syringe 28. Inside chamber 10, which is at high temperature, the sample vaporizes and all or part of it is conveyed to the gas chromatography column by the carrier.

Figure 2:
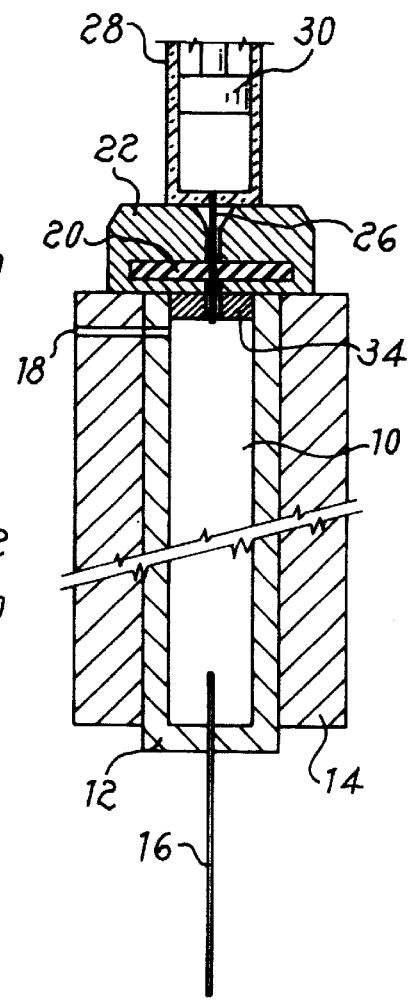
FIG. 2 is a schematic representation of an injection and vaporization device in accordance with a first embodiment of this invention

In the embodiment shown in FIG. 2, in accordance with the invention, the needle 26 of syringe 28 has a shorter length than those used in the known technique, for example a length such that the tip of the needle, under sample introduction conditions, only penetrates into vaporization chamber 10 for a limited distance.

Figure 4:
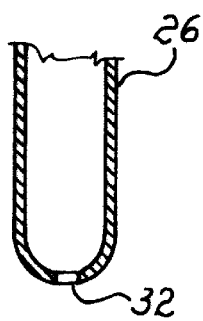
FIG. 4 is an enlarged schematic cross-section of the tip of a needle designed to implement this invention.

In addition, the head of needle 26 is shaped, for example, as illustrated in FIG. 4, in such a way as to present at least one terminal constriction 32 able to nebulise the liquid sample at the entrance to vaporization chamber 10 when the sample is pushed by plunger 30 of syringe 28.

Figure 5:
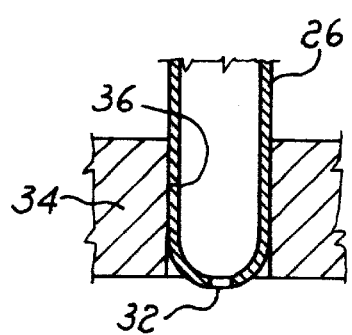
FIG. 5 is an enlarged schematic cross-section of the tip of the needle shown in FIG. 4, in conditions of introduction of the sample in accordance with the embodiment of this invention as shown in FIG. 2.

To improve the nebulisation conditions, the sample is injected in accordance with the needle preheating technique. This preheating can be enhanced, for example, by a metal block 34 (FIGS. 2 and 5) placed at the entrance of the vaporization chamber 10, and having a guide 36 for the tip of needle 26. Block 34 is heated from the outside by transfer of heat from vaporization chamber 10, or possibly by its own heating means, and guide 36 is dimensioned so as to allow the transmission of heat by conduction to the tip of needle 26. In this way nebulisation is improved due to the combination of mechanical and thermal effects, and because the solvent vaporizes instantly (flash vaporization) and acts as propellant for expulsion of the sample from the needle. In this case, the length of the needle particularly heated is basically the same as that of guide 36 (approx. 30 mm) plus a length of tip protruding from chamber 10 for approximately 2–10 mm.

Figure 3:
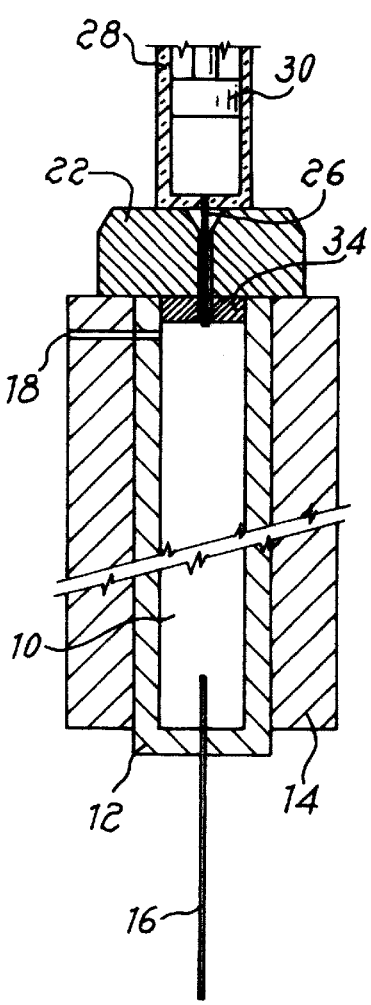
FIG. 3 is a schematic representation of an injection and vaporization device in accordance with a second embodiment of this invention.

In FIG. 2, the injector has an ordinary septum 20. In a second embodiment of this invention, the septum (which can be a source of problems, as described above) has been eliminated, and a seal is foreseen between the tip of needle 26 and guide 36 in block 34, as schematically illustrated in FIG. 3, which is sufficient to counteract the pressure of the sample created during injection. The seal can be formed by suitably dimensioning the coupled areas, or possibly by a suitable gasket on guide 36, made of a material resistant to the high temperatures in the chamber (e.g. Vespel).

Figure 6:
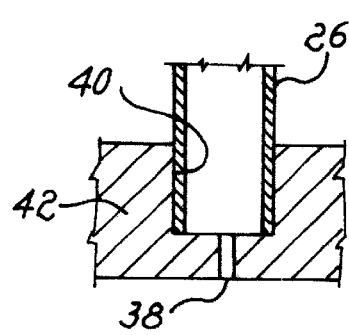
FIG. 6 is an enlarged schematic cross-section of another embodiment of this invention which constitutes an alternative to the one shown in FIG. 5.

In the first embodiment, the constriction 32 is at the tip of needle 26 which penetrates through the heated block 34. In the second embodiment of the invention, in which the block is heated, one or more constrictions 38 can be formed at the end of a guide 40 made in a specially shaped block 42, as shown in FIG. 6. In this case, needle 26 will have a tip of traditional configuration, and the coupling between the needle tip and guide 40 will be sealed to ensure a complete passage of the sample into chamber 10 and allow elimination of the septum. Also in the case of elimination of the septum, a constriction 38 can advantageously be used to produce a well-defined, limited leakage of carrier at the end of the injection which provides natural flushing of the injection area as it is permanently hot. This flushing means that there will be no contamination in subsequent injections, and also serves to clean the vaporization chamber after the sample has been introduced into the column, replacing discharge through the splitting output.

Sample injection systems other than the classic syringe with needle could be used as an alternative to the illustrated embodiments, such as a tube with valve systems designed to measure a predetermined quantity of liquid sample, connected to a pressure source to convey the liquid to the vaporization chamber. This tube, which could be permanently installed, would have the bottom end exactly corresponding to and operating in the same way as the tip of needle 26 in FIGS. 5 and 6, and could be constrained, perhaps permanently, to heating block 34 or 42 and possibly washed by countercurrent passage of carrier through it after introduction of the sample into the column.

What is claimed is:

1. A method for split-splitless injection of samples into a vaporizer of a gas chromatography analysis apparatus, comprising penetrating the needle of a syringe or the end of a tube designed for introduction of a sample into a vaporization chamber at high temperature, activating the plunger of the syringe or tube to force the sample into the vaporization chamber, the improvement comprising causing a nebulisation of the sample at the entrance to the vaporization chamber by at least one constriction in a passage through which the sample is conveyed from the interior of the needle or tube to the interior of the vaporization chamber.

2. A method as claimed in claim 1, wherein the nebulisation is effected by introducing the sample through one or more constrictions at a tip of the needle or tube.

3. A method as claimed in claim 1, wherein the nebulisation is effected by introducing the sample through one or more constrictions in a passage in the vaporization chamber, to which the tip of the needle or tube is sealingly coupled.

4. A method as claimed in claim 3, in a vaporization chamber without septum, further comprising forming a seal between the body of the needle and the passage until the transfer of the sample to the gas chromatography column has been completed.

5. A method as claimed in claim 2, further comprising heating a final portion of the tip of the needle or tube, having a length of 5 to 30 mm, before injection.

6. A method as claimed in claim 5, wherein the final portion of the tip of the needle or tube is heated by conduction by at least one heated metal block, which has a seat for the tip of needle or the end of tube.

7. A method as claimed in claim 6, wherein the metal block defines said passage having one or more constrictions.

8. A device for the injection of samples into a split-splitless vaporizer designed for a gas chromatography analysis apparatus, comprising a vaporization chamber maintained at high temperature, a syringe fitted with a needle or a tube, and a guide to introduce a tip of the needle into the vaporization chamber or means to position an end of the tube in the vaporization chamber, the improvement comprising providing at least one constriction through which the liquid passes at the entrance to the vaporization chamber between the inside of the needle or tube and said vaporization chamber.

9. A device as claimed in claim 8, wherein the at least one constriction is in the tip of the needle or the tube.

10. A device as claimed in claim 8, wherein the at least one constriction is in a passage in the vaporization chamber having a seat forming a sealed coupling with the tip of needle or tube.

11. A device as claimed in claim 9 or 10, wherein the terminal part of the needle or tube is in contact with a metal block containing a passage for said terminal part of the needle or tube, with an opening towards the vaporization chamber, said metal block being heated.

12. A device as claimed in claim 11, wherein the metal block is positioned in the initial part of the vaporization chamber and heated independently or by the atmosphere of said vaporization chamber.

13. A device as claimed in claim 11, further comprising a guide including stop means designed to limit the terminal part of the needle or tube which passes through the passage in the heated metal block and projects into the vaporization chamber to a segment between 2 and 10 mm long.

14. A device as claimed in claim 11, wherein one or more constrictions are present in an opening of said metal block.

15. A device as claimed in claim 11, wherein the seating of the metal block includes sealing means towards the tip of the needle or tube and in that the guide for introduction of the needle or tube has no septum.

16. A device as claimed in claim 14, wherein the at least one constriction in the metal block includes a passage to supply a carrier gas flushing flow through the opening in the block after introduction of the samples.

17. A method as claimed in claim 6, wherein the metal block defines said passage having one or more constrictions.

18. A device as claimed in claim 11, wherein the seating of the metal block includes sealing means towards the tip of the needle or tube and in that the guide for introduction of the needle or tube has no septum.

19. A device as claimed in claim 15, wherein the at least one constriction in the metal block includes a passage to supply a carrier gas flushing flow through the opening in the block after introduction of the samples.

20. A device as claimed in claim 18, wherein the at least one constriction in the metal block includes a passage to supply a carrier gas flushing flow through the opening in the block after introduction of the samples.

21. A device as claimed in claim 10, wherein the terminal part of the needle or tube is in contact with a metal block containing a passage for said terminal part of the needle or tube, with an opening towards the vaporization chamber, said metal block being heated.

22. A device as claimed in claim 21, wherein the metal block is positioned in the initial part of the vaporization chamber and heated independently or by the atmosphere of said chamber.

23. A method as claimed in claim 1, wherein the at least one constriction is between the interior of the needle and the interior of the vaporization chamber.

* * * * *